United States Patent
Nakagawa

[11] Patent Number: 5,997,142
[45] Date of Patent: Dec. 7, 1999

[54] EYE TEST METHOD USING RED AND GREEN MARKS AND RED/GREEN TESTER USED IN THE EYE TEST METHOD

[76] Inventor: Akio Nakagawa, 443-1, Fukakusa-okamedani-manjojiki-cho, Fushimi-ku, Kyoto-shi, Kyoto-fu, Japan

[21] Appl. No.: 09/125,694
[22] PCT Filed: Dec. 22, 1997
[86] PCT No.: PCT/JP97/04754
  § 371 Date: Aug. 24, 1998
  § 102(e) Date: Aug. 24, 1998
[87] PCT Pub. No.: WO98/27862
  PCT Pub. Date: Jul. 12, 1998

[30] Foreign Application Priority Data

Dec. 24, 1996 [JP] Japan ..................... 8-355958

[51] Int. Cl.[6] .................................................. A61B 3/10
[52] U.S. Cl. .................................................. 351/221
[58] Field of Search .................... 351/200, 205, 351/211, 212, 221, 246, 247, 233, 239, 243

[56] References Cited

U.S. PATENT DOCUMENTS

| | | | |
|---|---|---|---|
| 4,660,945 | 4/1987 | Trachtman | 351/205 |
| 5,684,561 | 11/1997 | Yancey | 351/211 |
| 5,914,772 | 6/1999 | Dyer | 351/246 |

*Primary Examiner*—George Manuel
*Attorney, Agent, or Firm*—Fish & Richardson, P.C.

[57] ABSTRACT

A red/green test apparatus for determining whether spectacle lenses or contact lenses are under-correcting or over-correcting has a case 1. The case 1 is divided into left and right parts by a partitioning plate 2 and a lamp 3R for red and a lamp 3G for green are disposed to the left and right of this partitioning plate 2; and a red film 5 is provided on the left side of the partitioning plate 2 and also a green film 6 is provided on the right side of the partitioning plate 2, both via an opalescent screen 4 on a front surface of the case 1. Two visual fixation marks 8 and 9 of identical shape and size form black displays at positions on the front surfaces of the films 5 and 6 corresponding to the lamps 3R and 3G, and a switching circuit is provided to cause the lamp 3G to either light or flicker for a fixed time, then cause the lamp 3G and the lamp 3R to light simultaneously. This makes it possible to perform a red/green visual target test in a state in which the unconscious accommodation of the crystalline lens performed by the test subject is suppressed as far as possible.

22 Claims, 5 Drawing Sheets

EYE TEST METHOD USING RED AND GREEN MARKS AND RED/GREEN TESTER USED IN THE EYE TEST METHOD

TECHNICAL FIELD

The present invention relates to an eye-testing method for determining under-correction and over-correction of spectacle lenses or contact lenses, while distinguishing between far-sightedness, normal vision, and near-sightedness, and a red/green test apparatus using that method.

BACKGROUND ART

A known eye-testing method for determining under-correction and over-correction of spectacle lenses or contact lenses, while distinguishing between far-sightedness, normal vision, and near-sightedness, disposes in a side-by-side arrangement a red visual target that displays a viusal fixation mark shaped as a black cross (plus sign) or a circle on a red background as well as a green visual target that displays a visual fixation mark identical to that of the red visual target on a green background, so that the test subject can see both targets simultaneously. This testing method makes use of chromatic aberration of the eye, using the fact that the difference in wavelengths between the red light and green light causes a displacement of the positions at which each of the red light and the green light come to a focus.

This testing method is described below.

When parallel reference rays of white light enter the eye through the crystalline lens thereof and come to a focus on the retina thereof, red light rays of a long wavelength are focused at a focal point behind the retina and green light rays of a short wavelength are focused at a focal point in front of the retina. In this state, because the distances of the focal point for red light and the focal point for green light from the retina are substantially equal, the visual fixation marks on the red and green backgrounds appear to have the same level of clarity. In other words, with a normal-sighted eye or optically-corrected eye, in theory the fixation marks of the red visual target and the green visual target appear approximately the same.

With a near-sighted eye, however, the reference light that has come from a distance is focused at a focal point which is in front of the retina, as will be described later with reference to the drawings, and thus the focal point for red light is closer to the retina than the focal point for green light, so that the fixation mark for the red visual target appears clearer than the fixation mark for the green visual target.

With a far-sighted eye which does not have the ability of accommodation, on the other hand, the reference light (parallel light) that has come from a distance is focused at a focal point which is behind the retina, as will be described later with reference to the drawings. When such an eye views the targets, the difference in wavelength causes that the focal point for the green light is closer to the retina than the focal point for red light, so the fixation mark for the green visual target appears clearer than the fixation mark for the red visual target.

In physical optics, the above theory holds for an eye without a crystalline lens after a cataract operation, an eye into which a lens has been inserted, and an eye of an elderly person of 70 years or more who has virtually no accommodation.

In physiological optics, however, it is rare for a far-sighted or normal-sighted eye with accommodation powers to see in accordance with the above theory.

This is because the human eye is constantly performing accommodation of the crystalline lens so that it is not fixed as in an artificial physical optical system. Since the human eye is focussing on objects in the outer world at a limited distance both physiologically and defensively, from the instant at which the eye opens, it is usual for even a far-sighted eye to cause the crystalline lens thereof to swell to focus on objects that the human wishes to see, at the instant at which the eye opens (within 0.5 to 1 second). In other words, a test subject is capable of clearly seeing both of the fixation marks of the red and green visual targets, by adjusting the crystalline lens unconsciously.

In addition, there is a tendency for the crystalline lens to retain this swelling state, which is an accommodation-rest state, rather than to retain a non-accommodated state (an alert state). Therefore, in most cases, both a normal-sighted eye and a far-sighted eye will tend to see the fixation mark of the red target more clearly.

At present, it is common to include red and green visual targets in an eye-chart for distance vision (5 meters), based on generic standards of the International Congress of Ophthalmology, but red and green visual targets have been virtually unused for a long time in ocular refraction testing, and, even when they are used, they are merely nominal since the determination thereof is unreliable. However, the spreading popularity of contact lenses in recent years is making it common for red and green visual targets to be used during the selection of contact lenses recently, starting with a check for over-correction by red and green viusal targets that is performed during the final stages of filling out a contact lens prescription.

However, as described above, the fixation mark of the red visual target tends to be seen clearly even with an over-corrected eye, so that easy use of red and green visual targets leads to problems such as a worsening in near-sightedness caused by over-correction of contact lenses and spectacles, and also an extremely high probability of causing VDT fatigue.

The present invention was devised in order to solve the above described problems, and thus an object thereof is the provision of an eye-testing method and an eye-testing apparatus using that method, wherein red and green visual targets are used in a state in which the unconscious accommodation of the crystalline lens performed by the test subject is suppressed as far as possible.

DISCLOSURE OF INVENTION

The present invention provides an eye-testing method comprising a step of showing a green visual target for a fixed time to a test subject; and a subsequent step of showing the green visual target and a red visual target simultaneously; whereby tendencies in ocular refraction and whether or not spectacle lenses or contact lenses that are worn are appropriate can be determined by causing the test subject to compare the green visual target and the red visual target.

Another aspect of this invention provides an eye-testing method comprising a step of showing a first green visual target for a fixed time to a test subject; and a subsequent step of showing a second green visual target and a red visual target simultaneously; whereby tendencies in ocular refraction and whether or not spectacle lenses or contact lenses that are worn are appropriate can be determined by causing the test subject to compare the second green visual target and the red visual target.

A further aspect of this invention provides an eye-testing method comprising a step of showing a visual target of a color having a wavelength shorter than that of green for a fixed time to a test subject; and a step of showing a green visual target and a red visual target simultaneously, after the first mentioned target has been extinguished; whereby tendencies in ocular refraction and whether or not spectacle lenses or contact lenses that are worn are appropriate can be determined by causing the test subject to compare the green visual target and the red visual target.

A still further aspect of this invention provides an eye-testing apparatus comprising a red visual target; a green visual target; and a switching circuit having means for causing the green visual target to light for a fixed time and means for causing the red visual target and the green visual target to light simultaneously, after the first mentioned lighting.

A yet further aspect of this invention provides an eye-testing apparatus comprising a first green visual target; a red visual target; a second green visual target; and a switching circuit having means for causing the first green visual target to light for a fixed time and means for causing the red visual target and the second green visual target to light simultaneously, after the first mentioned lighting.

A final aspect of this invention provides an eye-testing apparatus comprising a visual target of a color having a wavelength shorter than that of green; a red visual target; a green visual target; and a switching circuit having means for causing the target of a color having a wavelength shorter than that of green to light for a fixed time and means for causing the red visual target and the green visual target to light simultaneously, after the first mentioned lighting.

BEST MODE FOR CARRYING OUT THE INVENTION

Before describing actual embodiments of the present invention, the description first concerns problems related to tests using a red visual target and a green visual target, with reference to the accompanying drawings, in order to make the technical background of this invention clearer.

Figure 10:
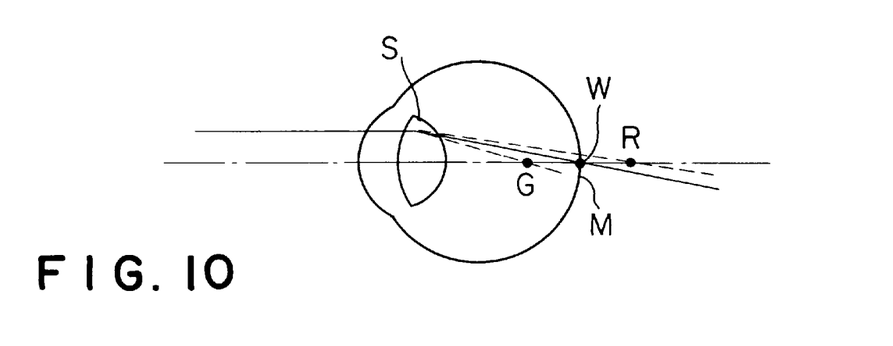
FIG. 10 is an illustrative view of focal points in a normal-sighted eye.

As shown in FIG. 10, when parallel reference rays of white light (strictly speaking, yellow light of a wavelength in the vicinity of 590 nm) enter an eye through the crystalline lens S thereof and come to a focus at a focal point W on the retina M thereof, red light rays of a long wavelength are focused at a focal point R behind the retina M and green light rays of a short wavelength are focused at a focal point G in front of the retina M. In this state, because the distances of the focal point R for red light and the focal point G for green light from the retina M are substantially equal, the visual fixation marks on the red and green background appear to have the same level of clarity. In other words, with a normal-sighted eye or optically-corrected eye, in theory the fixation marks of the red visual target and the green visual target appear approximately the same.

Figure 11:
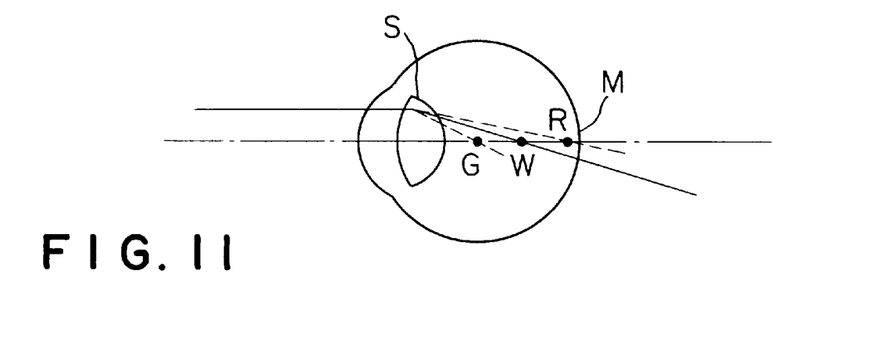
FIG. 11 is an illustrative view of focal points in a near-sighted eye.

With a near-sighted eye, however, the reference light (parallel light) that has come from a distance is focused at the focal point W which is in front of the retina M, so that the focal point R for red light is closer to the retina M than the focal point G for green light, as shown in FIG. 11. This means that in theory the fixation mark for the red visual target appears clearer than the fixation mark for the green visual target.

Figure 12:
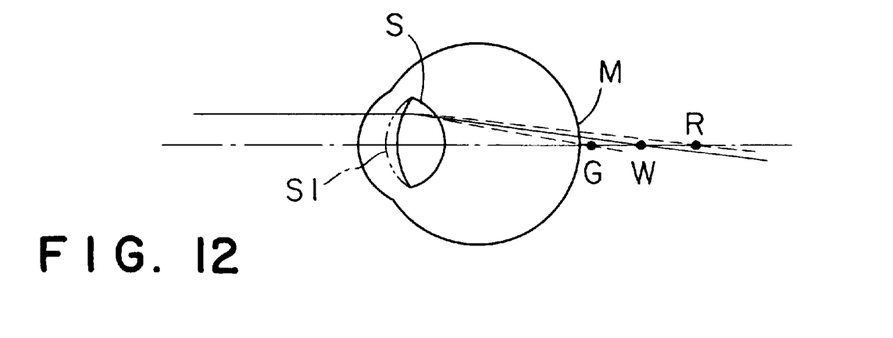
FIG. 12 is an illustrative view of focal points in a far-sighted eye.

With a far-sighted eye which does not have the ability of accommodation (there is absolutely no swelling of the crystalline lens), the reference light (parallel light) that has come from a distance is focused at the focal point W which is behind the retina M, as shown in FIG. 12. When such an eye looks into the distance (at a target 5 meters away), the difference in wavelength causes that the focal point G for green light is closer to the retina M than the focal point R for red light, so in theory the fixation mark for the green visual target appears clearer than the fixation mark for the red visual target.

In physical optics, the above theory holds for an eye without a crystalline lens after a cataract operation, an eye into which a lens has been inserted, and an eye of an elderly person of 70 years or more who has virtually no accommodation.

In physiological optics, however, it is rare for a far-sighted or normal-sighted eye with accommodation powers to see in accordance with the above theory.

This is because the human eye is constantly performing accommodation of the crystalline lens so that it is not fixed as in an artificial physical optical system. The focal point W for the white reference light when a far-sighted eye is not performing accommodation and is in a state in which the crystalline lens is completely non-accommodating (flat as a pancake) is at the position shown in FIG. 12, but the human eye is focussing on objects in the outer world at a limited distance both physiologically and defensively, from the instant at which the eye opens, so it is usual for even a far-sighted eye to cause the crystalline lens thereof to swell, as shown by the broken line S1 in FIG. 12, to focus on objects that the human wishes to see, at the instant at which the eye opens (within 0.5 to 1 second). In other words, a test subject is capable of clearly seeing both of the fixation marks of the red and green visual targets, by adjusting the crystalline lens unconsciously.

In addition, there is a tendency for the crystalline lens to retain a swelling of approximately 1.0 D (diopter) in an accommodation-rest state, rather than to retain a non-accommodated state (an alert state). Therefore, in most cases, both a normal-sighted eye and a far-sighted eye will tend to see the fixation mark of the red target more clearly.

At present, it is common to include red and green visual targets in an optical refraction chart for distance (5 meters) vision, based on generic standards of the International Congress of Ophthalmology, but red and green visual targets have been virtually unused for a long time in ocular refraction testing, and even when they are used, they are merely nominal since the determination thereof is unreliable. However, the spreading popularity of contact lenses in recent years is making it common for red and green visual targets to be used during the selection of contact lenses recently, starting with a check for over-correction by red and green visual targets that is performed during the final stages of filling out a contact lens prescription.

However, as described above, the fixation mark of the red visual target tends to be seen clearly even with an over-corrected eye, so that easy use of red and green visual targets leads to problems such as a worsening in near-sightedness caused by over-correction of contact lenses and spectacles, and also an extremely high probability of causing VDT fatigue.

The present invention, which is capable of solving the above described problems, will now be described in detail.

First Embodiment

Figure 1:
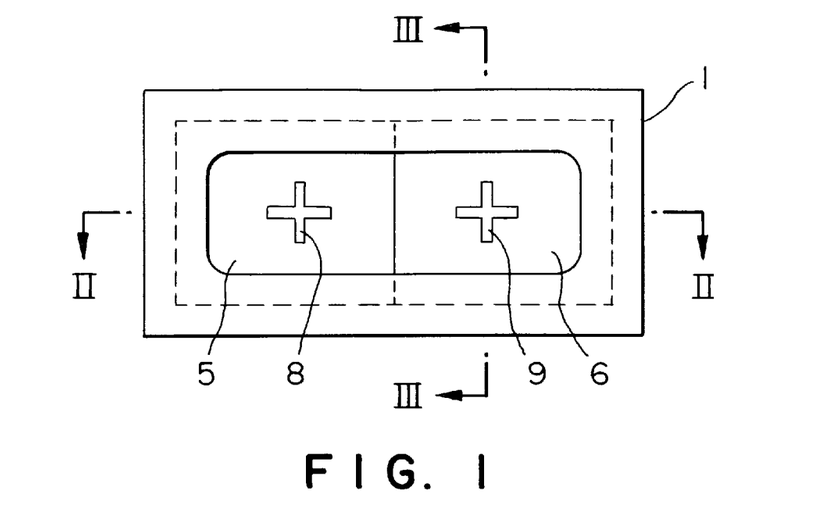
FIG. 1 is a front view of a first embodiment of the red/green test apparatus of the present invention.
Figure 2:
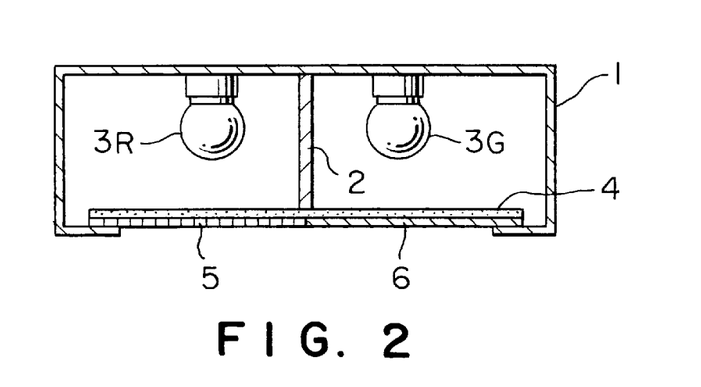
FIG. 2 is a sectional view taken along the line II—II of FIG. 1.
Figure 3:
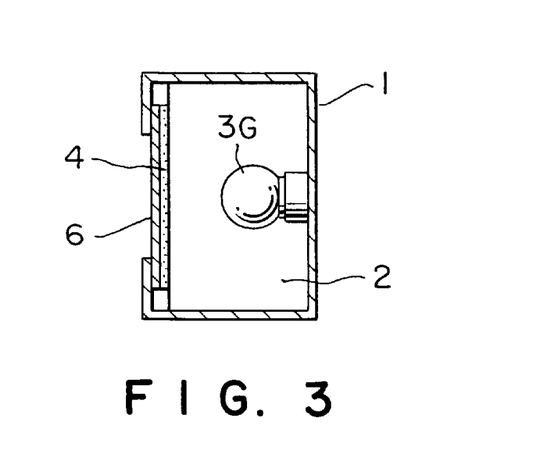
FIG. 3 is a sectional view taken along the line III—III of FIG. 1.
Figure 4A:
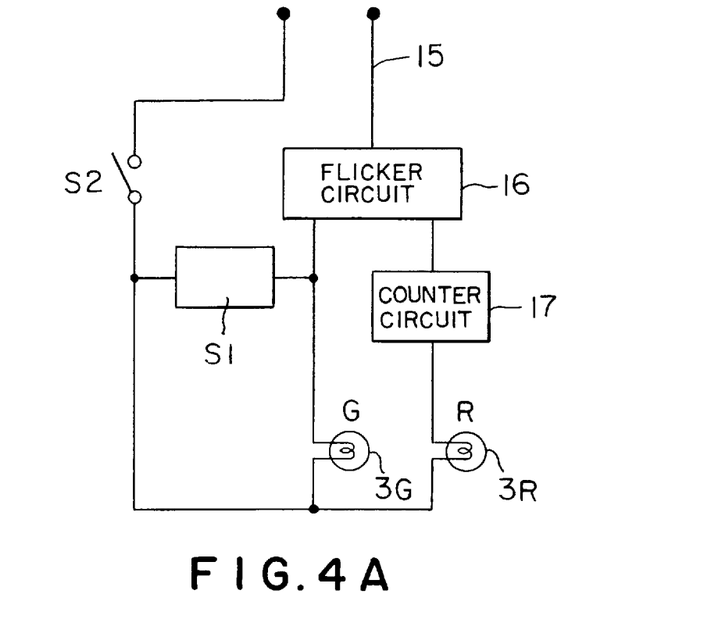
FIG. 4A shows a switching circuit of the red/green test apparatus of FIG. 1.

A first embodiment of the red/green test apparatus in accordance with this invention is shown in FIGS. 1 to 3. This red/green test apparatus has a case 1 of a shape that is rectangular and horizontally elongated, and the interior of this case 1 is divided into left and right chambers by a partitioning plate 2. Lamps 3R and 3G are supported on rear walls of the left and right chambers. An aperture is provided in the front surface of the case 1 and this aperture is covered with a composite sheet comprising an opalescent screen 4 with a red film 5 and a green film 6. The red film 5 is provided on the left side of the partitioning plate 2 and the green film 6 is provided on the right side of this partitioning plate 2, on the front surface of the opalescent screen 4. Black fixation visual marks 8 and 9 in the shape of fat crosses (plus signs) of equal size are implemented in the front surface of the films 5 and 6 at positions corresponding to the lamps 3R and 3G. As shown in FIG. 4, this red/green test apparatus is provided with a switching circuit that will be described later, for causing the lamp 3G for green light to light up or flicker continuously for a fixed time, then causing the lamp 3R for red light and the lamp 3G for green light to light simultaneously.

Note that, in this red/green test apparatus, the surface of the red film 5 wherein the fixation mark 8 is displayed in black constitutes a red visual target and the surface of the green film 6 wherein the fixation mark 9 is displayed in black constitutes a green visual target.

Instead of black displays, these fixation marks 8 and 9 in the shape of fat crosses (plus signs) could equally well be configured by cutting fat crosses (plus signs) out of black non-transparent film and arranging this black non-transparent film so that it is adhered to the front surfaces of the red film 5 and the green film 6. With such a configuration, the fixation mark 8 itself will be displayed in red and the fixation mark 9 itself will be displayed in green.

The flickering of the lamps in this first embodiment of the invention is performed by the switching circuit shown in FIG. 4A. In this switching circuit, a flicker circuit 16 is provided in an electrical circuit 15 which is equipped with a main switch S2; the lamps 3R and 3G are connected in series with this flicker circuit 16 so as to be mutually in parallel; a pulse counter circuit 17 is provided between the lamp 3R and the flicker circuit 16; and a manual or automatic switching device S1 is provided between the lamp 3G and the flicker circuit 16 and between the lamp 3G and the main switch S2, to light the lamp 3G continuously when switched on and flicker the lamp 3G when switched off.

Figure 4B:
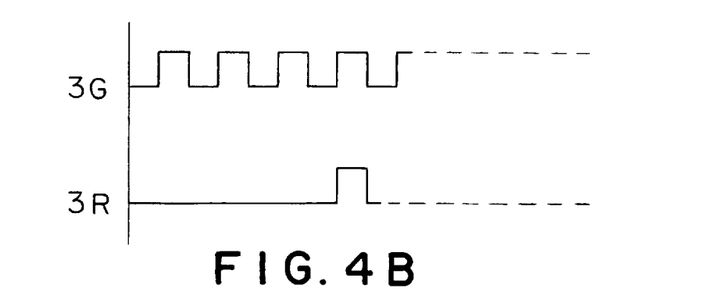
FIG. 4B is a timing chart illustrating the operation of the switching circuit of FIG. 4A.
Figure 4C:
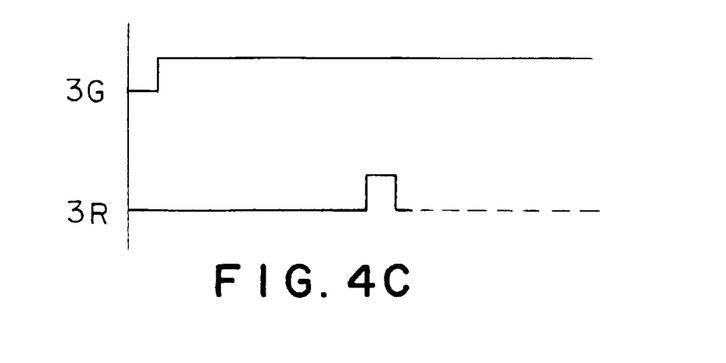
FIG. 4C is a timing chart illustrating an alternative operation of the switching circuit of FIG. 4A.

This flicker circuit 16 causes the generation of pulses such as those indicated by 3G in FIG. 4B, and it can adjust the pulse period and the pulse continuation timing. In addition, the pulse counter circuit 17 can modify the count of pulses, and, when it has counted a set number of pulses, it lights the lamp 3R once only as indicated by 3R in FIG. 4B. Note that the lamp 3G could also be lit continuously for a fixed period of time, as indicated by 3G in FIG. 4C.

Therefore, this switching circuit is capable of making the lamp 3G light or flicker continuously, and during that time it can cause the lamp 3R to light for predetermined short periods of time.

Second Embodiment

Figure 5:
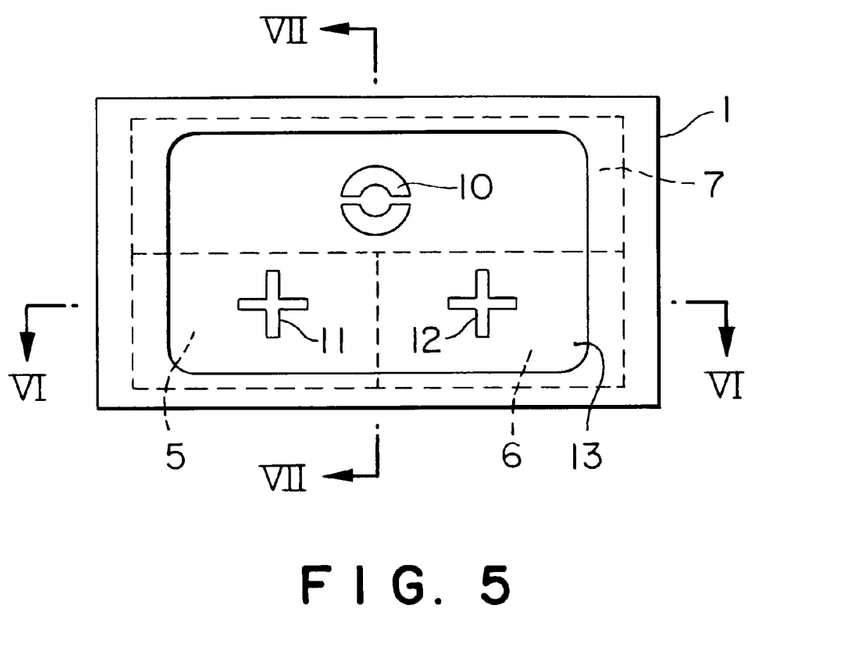
FIG. 5 is a front view of a second embodiment of the red/green test apparatus of the present invention.
Figure 6:
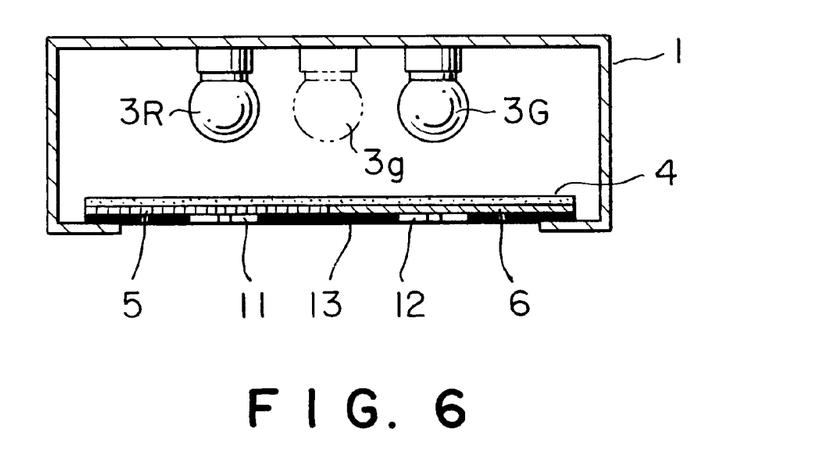
FIG. 6 is a sectional view taken along the line VI—VI of FIG. 5.
Figure 7:
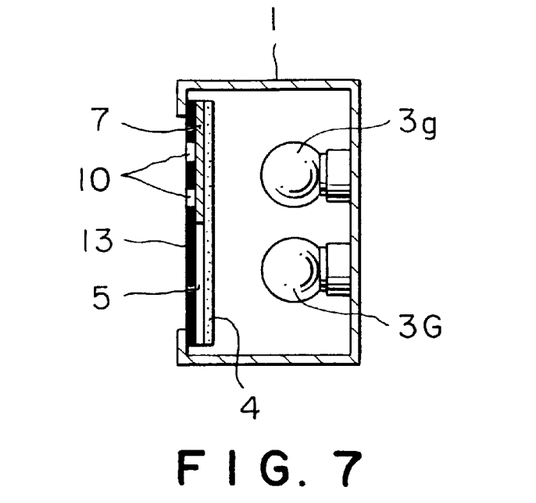
FIG. 7 is a sectional view taken along the line VII—VII of FIG. 5.

A second embodiment of the red/green test apparatus of this invention is shown in FIGS. 5 to 7. This red/green test apparatus has a case 1 of a shape that is rectangular and horizontally elongated and three lamps 3g, 3R, and 3G are provided in the upper center, lower left, and lower right of this case 1. The lamp 3g acts as a first green lamp and the lamp 3G acts as a second green lamp. These lamps are attached to a back wall within the case 1. An aperture on the front surface of the case 1 is covered with a composite sheet comprising an opalescent screen 4. A green film 7 is affixed to the front surface of the opalescent screen 4 in front of the upper central lamp 3g, and a red film 5 and a green film 6 are affixed thereto in front of the lower left and right lamps 3R and 3G, respectively. In addition, a black non-transparent film 13 is disposed attached to on the front surfaces of the films 5, 6, and 7, wherein the shape of a fat circle is cut out at a position corresponding to the lamp 3g and also the shapes of fat crosses (plus signs) of equal size are cut out at positions corresponding to the lamps 3R and 3G. This causes the fat circle shape to be displayed green as a first fixation mark 10 and the shapes of fat crosses (plus signs) to be displayed red at a fixation mark 11 as well as green at a fixation mark 12 as second fixation marks 11 and 12. In this red/green test apparatus, a switching circuit is provided to cause the upper central lamp 3g to light or flicker for a fixed period of time, then that lamp is turned off and the lower left and right lamps 3R and 3G are made to light simultaneously.

Note that, in this red/green test apparatus, the second fixation mark 11 itself that is displayed as red acts as a red visual target and the second fixaiton mark 12 itself that is displayed as green acts as a green visual target.

The fat circular fixation mark 10 and fixation marks 11 and 12 in the shape of fat crosses (plus signs) need not be cut out of the black non-transparent film 13, and they could black displays on the front surfaces at positions corresponding to the films 5, 6, and 7, in a similar manner to that of the above described first embodiment. Note that a film of a color having a wavelength shorter than that of green (such as purple, indigo, or blue) could be used instead of the green film 7, to achieve the same effect as that described above.

Figure 8:
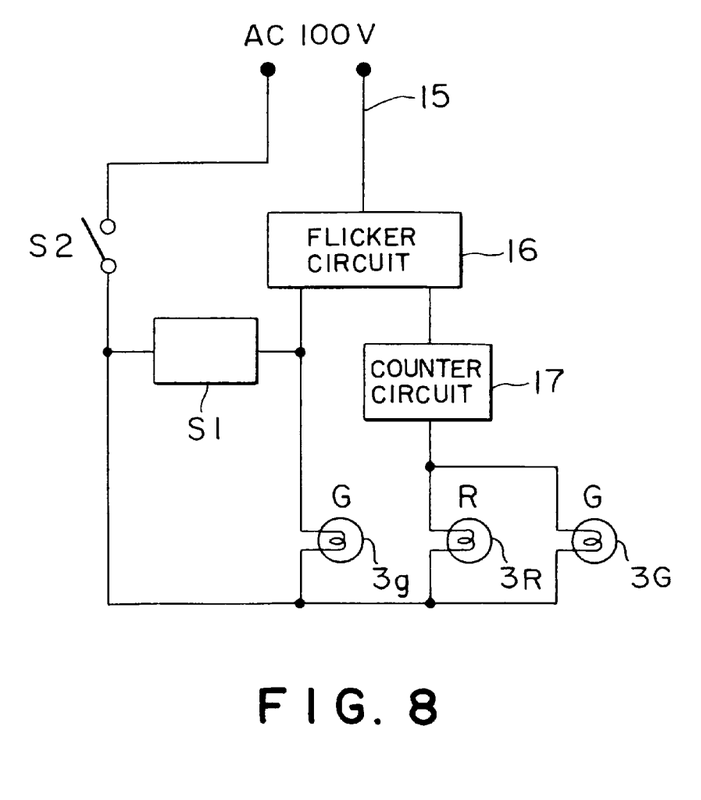
FIG. 8 shows a switching circuit of the red/green test apparatus of FIG. 5.

The flickering of the lamps in this second embodiment of the invention is performed by the switching circuit shown in FIG. 8. This circuit is basically the same as that of the above described first embodiment, with the differences being that the lamp 3g is disposed instead of the lamp 3G of FIG. 4A, and the lamp 3R is connected in parallel to the lamp 3G.

Thus, the lamp 3g can be made to light or flicker continuously by this circuit, or the lamps 3R and 3G can be made to light for a predetermined period of time after the lamp 3g has been extinguished.

Note that each of the red/green test apparatuses of the first and second embodiments can be set in the previously described eye-chart for distance vision (5 meters).

Figure 9:
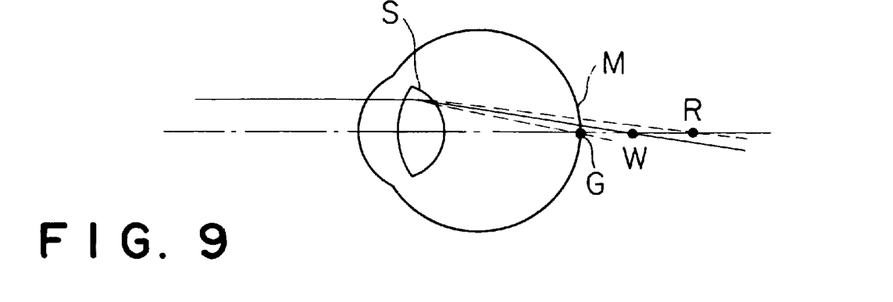
FIG. 9 is an illustrative view of focal points in a state in which a far-sighted eye is staring at a green visual target alone.

If the red/green test apparatus of the first or second embodiment is used and a test subject having a far-sighted eye or an over-corrected eye is made to stare at the green visual target alone, which is either flickering or lit continuously, the test subject will unconsciously adjust the crystalline lens so that, in either test apparatus, the green light G will be focused at the focal point G on the retina M, as shown in FIG. 9. After this state has continued for a few seconds, if the red visual target is lit for approximately 1 second and the test subject is made to see it, the focal point R will be closer to the retina M than the focal point G, so the red visual target will appear unclear. In this case, the red target is extinguished before the eye attempts to adjust the focal point towards the red-target side, so the eye once again focuses on the green target side. The occurrence of focal-point accommodation (adjustment of the crystalline lens) performed unconsciously by the test subject can be suppressed as far as possible by repeating this process and causing the test subject to compare (the targets). Note that the lamp 3R for red light is typically lit once after the lamp 3G for green light has been flashed three to seven times.

The description now turns to test examples in which the red/green test apparatus in accordance with the first embodiment was used for the testing method using a red visual target and a green visual target in accordance with this invention.

Note that HT024 (product of Lee Filters Ltd. of Great Britain) was used as the red film 5, HT124 (product of Lee Filters Ltd. of Great Britain) was used as the green film 6, and the dimensions of the fixation marks 8 and 9 were such that the width of the arms of the crosses (plus signs) was 1.5 mm and the lengths of the crosses (plus signs) in the vertical and horizontal directions was 20 mm. The brightness of the red and green visual targets was set to 800 cd/m$^2$.

TEST A

Conventional Method

The test subject was made to stare at the red and green targets in a state in which both of the targets were lit, as in the prior art, then was asked which of the fixation marks of the red and green targets appeared clearer.

TEST B

Method of this Invention

The test subject was made to stare at the green target alone in a lit state, the red target and the green target were lit simultaneously for one second in four seconds, and the test subject was asked which of the fixation marks of the red and green targets appeared clearer during that time.

TEST C

Method of this Invention

The green target was flickered for several seconds at a timing of one second lit and one second extinguished, then the red target was flickered at a timing of one second lit and four seconds extinguished, and subsequently both red and green targets were lit simultaneously; the test subject was asked which of the fixation marks of the red and green targets appeared clearer during that time.

The determination results obtained by these Tests A, B, and C are listed below. Note that in these results R stands for red and G stands for green, and the differences in viewing state are indicated by inequality signs.

Test Subject 1: Female, 24 Years Old, with Normal Sight
  i) With naked eyes (Note: Theoretically, red and green ought to appear at the same clarity)
    Test A: R>G (red was clearer); Test B: R=G (red and green appeared the same); Test C: R=G (red and green appeared the same)
  ii) The same test subject, placed in a far-sighted state by the wearing of concave lenses of Sph (spherical) −0.5 D (diopter) (Note: Theoretically, green ought to appear clearer)
    Test A: R>G; Test B: R<G (green was clearer); Test C: R<G (green was clearer)
  iii) The same test subject, placed in a near-sighted state by the wearing of convex lenses of Sph +0.5 D (Note: Naturally, red ought to appear clearer)
    Test A: R>G; Test B: R>G; Test C: R>G
Test Subject 2: Male, 26 Years Old, Short-Sighted (Sph +1.0 D)
  i) With naked eyes (Note: Theoretically, green ought to appear clearer)
    Test A: R>G; Test B: R<G; Test C: R<G
  ii) The same test subject, placed in a normal-sighted state by the wearing of convex lenses of Sph +1.0 D
    Test A: R>G; Test B: R=G; Test C: R=G
  iii) The same test subject, placed in a far-sighted state by the wearing of convex lenses of Sph +0.5 D (Note: The same result as i) above ought to be obtained)
    Test A: R>G; Test B: R<G; Test C: R<G
Test Subject 3: Female, 22 Years Old, Short-Sighted, Wearing Suitably Corrective Contact Lenses
  i) Wearing contact lenses (Note: Theoretically, red and green ought to appear the same)
    Test A: R>G; Test B: R=G; Test C: R=G
  ii) The same test subject, over-corrected (towards the far-sighted side) by concave lenses of Sph −0.5 D (Note: Theoretically, green ought to appear clearer)
    Test A: R>G; Test B: R<G; Test C: R<G
  iii) The same test subject, placed in a near-sighted state by the wearing of convex lenses of Sph +0.5 D (Note: Naturally, red ought to appear clearer)
    Test A: R>G; Test B: R>G; Test C: R>G
Test Subject 4: Female, 27 Years Old, Short-Sighted, Wearing Over-Corrective Contact Lenses (Main Complaint: Eyestrain)
  i) Wearing contact lenses (Note: Theoretically, green ought to appear clearer)
    Test A: R>G; Test B: R<G; Test C: R<G
As a result of refractive retesting, it was found that the contact lenses were over-corrective.
Test Subject 5: Male, 66 Years Old, Long-Sighted (Sph +0.75 D), With Substantially No Accommodation Due to Age
  i) With naked eyes (Note: Theoretically, green ought to appear clearer)
    Test A: R<G; Test B: R<G; Test C: R<G
  ii) Wearing completely corrected spectacle lenses
    Test A: R=G; Test B: R=G; Test C: R=G
From the above determination results it is clear that results close to theory were obtained for elderly people without accommodation powers in the crystalline lenses and for people having eyes without crystalline lenses wearing artificial lenses in the eyes, but the method of Test A could be said to be meaningless for people who do have powers of accommodation in the crystalline lenses.

A comparison of Tests B and C showed that no difference in effect was observed between the test results of B and C.

These tests were performed with the black fixation marks shown in FIG. 1, but even clearer diagnoses of the test subjects were obtained when they were performed with the cut-out fixation marks of FIG. 5 (the fixation marks themselves were red and green targets). This is thought to be because the eye is readily influenced by the visual sensitivity curves and the after-image effect when there is a colored background with a broad field of view.

When tests were performed on the above Test Subject 1, using the red/green test apparatus of the second embodiment wherein the test subject was shown the first fixation mark (green target) 10 in the upper center, either lit or flickering for five seconds, the mark was extinguished, then immediately the second fixation mark 11 (red target) and the second fixation mark 12 (green target) were lit simultaneously and the test subject was asked which of the fixation marks appeared clearer, the determination results were the same as those for the previous Tests B and C, but the responses of the test subject were more definite. This is thought to be because it is easier to decide when seeing new red and green fixation marks 11 and 12 simultaneously after seeing the fixation mark 10 in a completely different state.

Note that the red film 5 and the green films 6 and 7 that were used were the same as those used in the first embodiment; the dimensions of the first fixation mark were a thickness of 2 mm, an outer diameter of 10 mm, and the width of the central cut-out portion was 2 mm; and the dimensions of the fixation marks 11 and 12 were an arm width of 1.5 mm and a length in the vertical and horizontal directions of 20 mm.

The brightness of the first and second fixation marks was set to 800 cd/m2.

Since the present invention makes it possible to accurately determine whether or not the adjustment of spectacle lenses or contact lenses is appropriate, it enables the selection of the optimal spectacle lenses or contact lenses for the test subject.

The industrial applicability of the present invention is therefore extremely high.

I claim:

1. An eye-testing method comprising the steps of:
    showing a green visual target for a fixed time to a test subject; and
    subsequently showing said green visual target and a red visual target simultaneously;
    whereby tendencies in ocular refraction and whether or not spectacle lenses or contact lenses that are worn are appropriate are determined by causing said test subject to compare said green visual target and said red visual target.

2. The eye-testing method as defined in claim 1, wherein said step of showing a green visual target for a fixed time to a test subject is performed by causing said green visual target to flicker for a fixed time.

3. The eye-testing method as defined in claim 1, wherein said step of showing a green visual target for a fixed time to a test subject is performed by causing said green visual target to light continuously for a fixed time.

4. An eye-testing method comprising the steps of:
    showing a first green visual target for a fixed time to a test subject; and
    subsequently showing a second green visual target and a red visual target simultaneously;
    whereby tendencies in ocular refraction and whether or not spectacle lenses or contact lenses that are worn are appropriate are determined by causing said test subject to compare said second green visual target and said red visual target.

5. The eye-testing method as defined in claim 4, wherein said step of showing a first green visual target for a fixed time to a test subject is performed by causing said first green visual target to flicker for a fixed time.

6. The eye-testing method as defined in claim 4, wherein said step of showing a first green visual target for a fixed time to a test subject is performed by causing said first green visual target to light continuously for a fixed time.

7. An eye-testing method comprising the steps of:
    showing a visual target of a color having a wavelength shorter than that of green for a fixed time to a test subject; and
    showing a green visual target and a red visual target simultaneously, after said first mentioned visual target has been extinguished;
    whereby tendencies in ocular refraction and whether or not spectacle lenses or contact lenses that are worn are appropriate are determined by causing said test subject to compare said green visual target and said red visual target.

8. The eye-testing method as defined in claim 7, wherein said step of showing a target of a color having a wavelength shorter than that of green for a fixed time to a test subject is performed by causing said target to flicker for a fixed time.

9. The eye-testing method as defined in claim 7, wherein said step of showing a target of a color having a wavelength shorter than that of green for a fixed time to a test subject is performed by causing said target to light continuously for a fixed time.

10. An eye-testing apparatus comprising:
    a red visual target;
    a green visual target; and
    a switching circuit having means for causing said green visual target to light for a fixed time and means for causing said red visual target and said green visual target to light simultaneously, after said initial lighting.

11. The eye-testing apparatus as defined in claim 10, wherein said means of said switching circuit for causing said green visual target to light for a fixed time is means for causing said green visual target to light in a flickering state for a fixed time.

12. The eye-testing apparatus as defined in claim 10, wherein said means of said switching circuit for causing said green visual target to light for a fixed time is means for causing said green visual target to light continuously for a fixed time.

13. The eye-testing apparatus as defined in claim 10, wherein said red visual target comprises a lamp for red, a red film provided therebefore, and a black fixation mark provided on said red film; and said green visual target comprises a lamp for green, a green film provided therebefore, and a black fixation mark provided on said green film.

14. The eye-testing apparatus as defined in claim 13, wherein said red film and said green film are superimposed on an opalescent screen.

15. The eye-testing apparatus as defined in claim 10, wherein said red visual target comprises a lamp for red, a red film on a front surface thereof, a non-transparent film for red affixed to said red film, and a black fixation mark cut out of said non-transparent film for red; and said green visual target comprises a lamp for green, a green film on a front surface thereof, a non-transparent film for green affixed to said green film, and a black fixation mark cut out of said non-transparent film for green.

16. An eye-testing apparatus comprising:

a first green visual target;

a red visual target;

a second green visual target; and a switching circuit having means for causing said first visual green target to light for a fixed time and means for causing said red visual target and said second green visual target to light simultaneously, after the first mentioned lighting.

17. The eye-testing apparatus as defined in claim 16, wherein said means of said switching circuit for causing said first green visual target to light for a fixed time is means for causing said first green visual target to light in a flickering state for a fixed time.

18. The eye-testing apparatus as defined in claim 16, wherein said means of said switching circuit for causing said first green visual target to light for a fixed time is means for causing said first green visual target to light continuously for a fixed time.

19. The eye-testing apparatus as defined in claim 16, wherein said red visual target comprises a lamp for red, a red film provided therebefore, and a black fixation mark provided on said red film; and each of said first and second green visual targets comprises a lamp for green, a green film provided therebefore, and a black fixation mark provided on said green film.

20. The eye-testing apparatus as defined in claim 19, wherein said red film and said green films are superimposed on an opalescent screen.

21. The eye-testing apparatus as defined in claim 16, wherein said red visual target comprises a lamp for red, a red film on a front surface thereof, a non-transparent film for red affixed to said red film, and a black fixation mark cut out of said non-transparent film for red; and each of said first and second green visual targets comprises a lamp for green, a green film on a front surface thereof, a non-transparent film for green affixed to said green film, and a black fixation mark cut out of said non-transparent film for green.

22. An eye-testing apparatus comprising:

a visual target of a color having a wavelength shorter than that of green;

a red visual target;

a green visual target; and a switching circuit having means for causing said visual target of a color having a wavelength shorter than that of green to light for a fixed time and means for causing said red visual target and said green visual target to light simultaneously, after said first mentioned lighting.

* * * * *